US00PP09610P

United States Patent [19]

Leue

[11] Patent Number: Plant 9,610

[45] Date of Patent: Jul. 23, 1996

[54] IMPATIENS PLANT NAMED 'TROPICAL ORANGE'

[75] Inventor: Ellen F. Leue, West Chicago, Ill.

[73] Assignee: Geo J. Ball, Inc., West Chicago, Ill.

[21] Appl. No.: 445,372

[22] Filed: May 19, 1995

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 3,918 6/1976 Hope et al. ..... Plt./87.6

*Primary Examiner*—Howard J. Locker

*Attorney, Agent, or Firm*—Burns, Doane, Swecker & Mathis

[57] ABSTRACT

A new and distinct cultivar of Impatiens plant, botanically known as *Impatiens wallerana,* and named 'Tropical Orange' is provided. This new cultivar was the result of a controlled breeding program wherein a plant designated 447-1 (non-patented in the United States) was pollinated by a plant designated 52-2-1 (non-patented in the United States). The new cultivar is early blooming and forms in abundance attractive fully double orange blooms that possess a somewhat iridescent appearance. The foliage is dark green. The plant exhibits a good basal-branching character and exhibits a medium upright mounded growth habit. The new cultivar can be readily distinguished from the 'Rosebud Orange' cultivar (non-patented in the United States) in view of the more compact growth habit and slightly larger flowers that are provided.

1 Drawing Sheet

SUMMARY OF THE INVENTION

The present invention provides a new and distinctive Impatiens plant, botanically known as *Impatiens wallerana,* and hereinafter referred to by the cultivar name 'Tropical Orange'.

The new cultivar is the product of a planned breeding program. More specifically, the breeding program which resulted in the production of the new cultivar was carried out in a controlled environment during September, 1991, at Elburn, Ill., U.S.A. The female parent (i.e., the seed parent) was a plant designated 447-1 (non-patented in the United States) which exhibits lavender/rose semi-double flowers and medium green foliage. The male parent (i.e., the pollen parent) was a plant designated 52-2-1 (non-patented in the United States) which exhibits orange double flowers with medium green foliage. The parentage of the new cultivar can be summarized as follows:

447-1×52-1.

The seeds resulting from the above pollination were sown and plantlets were obtained which were physically and biologically different from each other. Selective study resulted in the identification of a single plant of the new cultivar. This plant had distinctive fully double orange blooms and initially was designated 759-2.

It was found that the new cultivar of the present invention:

(a) exhibits attractive fully double orange blooms in abundance,
(b) is early blooming,
(c) forms dark green foliage,
(d) exhibits a good basal-branching character, and
(e) exhibits a medium upright mounded growth habit.

Asexual reproduction of the new cultivar by stem cuttings taken during May and September, 1993, and during October, 1994, at Elburn, Ill., U.S.A., has demonstrated that the characteristics of the new cultivar as herein described are firmly fixed and are retained through succesive generations of such asexual propagation.

The 'Tropical Orange' cultivar has not been observed under all possible environmental conditions to date. Accordingly, it is possible that the phenotype may vary somewhat with variations in the environment, such as temperature, light intensity, and day length.

When the new cultivar of the present invention is compared to the 'Rosebud Orange' cultivar (non-patented in the United States), it is found that the new cultivar exhibits slightly large flowers (e.g., approximately 4.0 to 4.2 cm. in diameter vs. approximately 3.7 to 4.1 cm.), and a more compact habit (e.g., approximately 8.0 to 11.0 cm. in height×approximately 19.0 to 25.0 cm. in width vs approximately 17.0×21.0 cm. in height×approximately 25.0 to 29.0 cm. in width).

When plant material of the 'Tropical Orange' cultivar is subjected to standard random amplified polymorphic DNA marker analysis (RAPD) using polymerase chain reaction (PCR) and a known unique set of DNA primers, it is found to exhibit a different fingerprint map when compared to that of 'Rosebud Orange' cultivar which confirms its genetic distinctiveness.

Plants of the new cultivar will be marketed under the FIESTA trademark by Geo. J. Ball, Inc.

BRIEF DESCRIPTION OF THE PHOTOGRAPHS

The accompanying photographs show the new 'Tropical Orange' cultivar with colors being as nearly true as it is reasonably possible to make the same in color illustrations of this character. The plants were being grown in greenhouses at West Chicago, Ill. U.S.A.

DETAILED DESCRIPTION

Figures 1, 2:
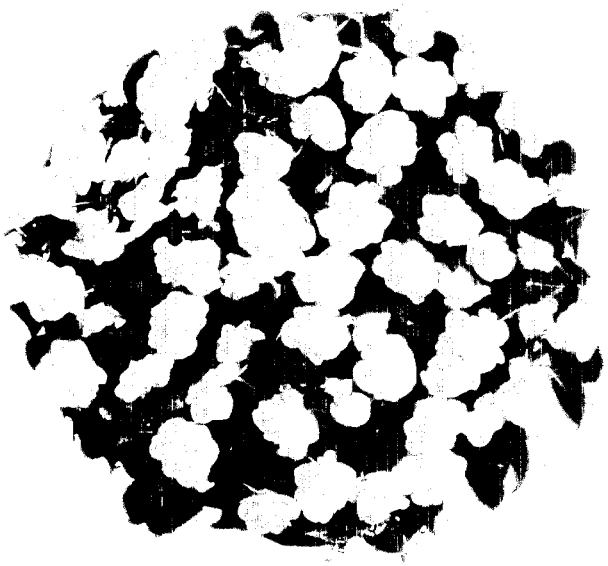
FIG. 1 illustrates the general appearance of an overall plant as seen primarily from above.
FIG. 2 illustrates the general appearance of a typical floret when subjected to bright light.

The chart used in the identification of colors described herein is the R.H.S. Colour Chart of The Royal Horticultural Society, London, England. The color values were determined on Jan. 3, 1995. The readings were taken between 10:00 and 11:00 a.m. under 2,000 footcandles of light at West Chigaco, Ill., U.S.A. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night.

Propagation:

*Type cutting.*—Two or three vegetative node stem cuttings from near the centers of the plants.

*Time to initiate roots.*—Approximately 7 to 14 days with the shorter times generally being experienced in the summer and the longer times in the winter.

*Rooting habit.*—Fibrous, and branching.

Plant description:

*Habit of growth.*—Basal-branching, and exhibits a medium upright mounted growth habit.

*Form.*—A mature plant at 8 weeks after the planting of a rooted cutting commonly measures approximately 8.0 to 11.0 cm. in height and approximately 19.0 to 25.0 cm. in width compared to approximately 17.0 to 21.0 cm. in height and approximately 25.0 to 29.0 cm. in width for the 'Rosebud Orange' cultivar.

*Foliage.*—The configuration is ovate with an acuminate tip. The leaves of the new cultivar commonly measure approximately 5.0 to 6.2 cm. in length and approximately 3.7 to 4.0 cm. in width while those of the 'Rosebud Orange' cultivar commonly measure approximately 5.5 to 6.5 cm. in length and approximately 3.6 to 4.5 cm. in width. The foliage of the new cultivar is Yellow-Green Group 146A (adaxial) and Yellow-Green Group 147C (abaxial). This can be compared to Green Group 137A (adaxial) and Green Group 137B (abaxial) for the 'Rosebud Orange' cultivar. The stem color is Green Group 143B with streaks of Greyed-Purple Group 185A which compares to Yellow-Green Group 144B for the 'Rosebud Orange' cultivar.

Flower description:

*Flowering habit.*—Freely flowering. Small round buds become more oval with maturity and flowers open in a rose-like fashion.

*Natural flowering season.*—Early blooming and blooms throughout the year in a greenhouse environment.

*Flowers borne.*—Slightly above the foliage.

*Flower color.*—Orange-Red Group 33B on fully opened petals with the central area of tightly packed petals of Orange-Red Group 33A (adaxial) and Orange-Red Group 33D (abaxial). Portions of the undersides of the bud petals may sometimes be lighter in coloration as illustrated in FIG. 1. This can be compared to Orange-Red Group 33B (adaxial) and Orange-Red Group 35B (abaxial) for the 'Rosebud Orange' cultivar.

*Quantity of flowers.*—Very floriferous. A mature plant commonly is totally covered with blooms.

*Number of petals.*—Fully double and petals commonly are too numerous to readily count.

*Petal shape.*—Round to oblong.

*Flower size.*—Approximately 4.0 to 4.2 cm. in diameter which can be compared to a diameter of approximately 3.7 to 4.1 cm. for the 'Rosebud Orange' cultivar.

*Spur.*—One per flower of approximately 3.5 to 3.6 cm. in length which can be compared to one per flower of approximately 3.4 to 3.7 cm. in length for the 'Rosebud Orange' cultivar.

*Spur color.*—Lighter than Orange-Red Group 33A for both the 'Tropical Orange' cultivar and the 'Rosebud Orange' cultivar.

*Reproductive organs.*—The stamens are multiple in number and the styles and ovaries are generally typical of the species and non-distinctive.

I claim:

1. A new and distinct cultivar of *Impatiens walerana* plant named 'Tropical Orange' substantially as herein shown and described, which:

(a) exhibits attractive fully double orange blooms in abundance,
(b) is early blooming,
(c) forms dark green foliage,
(d) exhibits a good basal-branching character, and
(e) exhibits a medium upright mounded growth habit.

* * * * *